United States Patent
Ma et al.

(10) Patent No.: US 8,735,310 B2
(45) Date of Patent: May 27, 2014

(54) METHOD OF REGENERATING LOWER HYDROCARBON AROMATIZING CATALYST

(75) Inventors: Hongtao Ma, Tokyo (JP); Yuji Ogawa, Kawagoe (JP)

(73) Assignee: Meidensha Corporation, Tokyo (JP)

( * ) Notice: Subject to any disclaimer, the term of this patent is extended or adjusted under 35 U.S.C. 154(b) by 581 days.

(21) Appl. No.: 12/594,902

(22) PCT Filed: Mar. 17, 2008

(86) PCT No.: PCT/JP2008/054883
§ 371 (c)(1),
(2), (4) Date: Oct. 6, 2009

(87) PCT Pub. No.: WO2008/149591
PCT Pub. Date: Dec. 11, 2008

(65) Prior Publication Data
US 2010/0137125 A1   Jun. 3, 2010

(30) Foreign Application Priority Data
Jun. 7, 2007  (JP) .............................. 2007-151272

(51) Int. Cl.
*C07C 15/02*   (2006.01)

(52) U.S. Cl.
USPC ............. 502/53; 585/402; 585/405; 585/411; 585/412; 585/418

(58) Field of Classification Search
CPC .................................. C07C 15/02; B01J 38/10
USPC ............................................. 502/53; 585/402
See application file for complete search history.

(56) References Cited

U.S. PATENT DOCUMENTS

2008/0249342 A1* 10/2008 Iaccino et al. ................ 585/402
2008/0312483 A1  12/2008 Ichikawa et al.

FOREIGN PATENT DOCUMENTS

| JP | 7-258658 A | 10/1995 |
| JP | 10-272366 A | 10/1998 |
| JP | 11-60514 A | 3/1999 |
| JP | 2003-026613 A | 1/2003 |
| JP | 2005-230644 A | 9/2005 |
| JP | 2005-254120 A | 9/2005 |

(Continued)

OTHER PUBLICATIONS

Methane Conversion to Aromatics on Mo/H-ZSM5:Structure of molybdenum Species in Working catalysts. Weiping Ding et al. Unversity of California at Berkerly. Oct. 2000.*

(Continued)

*Primary Examiner* — Melvin C Mayes
*Assistant Examiner* — Colette Nguyen
(74) *Attorney, Agent, or Firm* — Foley & Lardner LLP (57) ABSTRACT

To improve stability of catalytic performance, an aromatizing catalyst for converting lower hydrocarbons into aromatic compounds is regenerated. A regeneration process of the aromatizing catalyst according to the present invention includes the steps of: (a) reacting the aromatizing catalyst with a hydrogen gas in an atmosphere containing the hydrogen gas after using the aromatizing catalyst in an aromatizing reaction for converting lower hydrocarbons into aromatic compounds; (b) decreasing a temperature of the atmosphere containing the hydrogen gas reacted with the aromatizing catalyst, by supplying one of an inert gas and a reducing gas to the atmosphere; (c) reacting the aromatizing catalyst reacted with this inert gas, with an oxidizing gas; and (d) reacting the aromatizing catalyst reacted with the oxidizing gas, with a reducing gas.

4 Claims, 6 Drawing Sheets

(56) References Cited

FOREIGN PATENT DOCUMENTS

| | | |
|---|---|---|
| JP | 2005-254121 A | 9/2005 |
| JP | 2005-254122 A | 9/2005 |
| JP | 2005-255605 A | 9/2005 |
| JP | 2006-263682 A | 10/2006 |
| JP | 2006-263683 A | 10/2006 |
| JP | 2007-014894 A | 1/2007 |
| WO | WO 2005/028105 A1 | 3/2005 |
| WO | WO 2006/011568 A1 | 2/2006 |

OTHER PUBLICATIONS

Weiping Ding et al., Methane Conversion to Aromatics on Mo/H-ZSM5: Structure of Molybdenum Species in Working Catalysts, J. Phys. Chem. B, vol. 105, 2001, pp. 506-513.

F. Solymosi et al.., "Aromatization of Methane over Supported and Unsupported Mo-Based Catalysts", Journal of Catalysis, vol. 165 (1997), pp. 150-161.

* cited by examiner

METHOD OF REGENERATING LOWER HYDROCARBON AROMATIZING CATALYST

TECHNICAL FIELD

The present invention relates to a process of regenerating a catalyst for converting lower hydrocarbons into aromatic compounds, the process making it possible to efficiently produce: aromatic compounds whose main component is benzenes used as chemical industrial materials; and hydrogen used as a fuel for fuel cells, from methane-containing gases such as natural gas, bio gas and coke oven gas.

BACKGROUND TECHNIQUE

Catalysts that have been considered to be effective are those as disclosed in "JOURNAL OF CATALYSIS" (1997, vol. 165, pp. 150-161) and Japanese Patent Provisional Publications Nos. 10-272366 and 11-60514, in which the catalysts are capable of producing hydrogen and aromatic compounds such as benzene from methane in one stage.

However, the coke formation is still serious even if such catalysts are used, with which the catalytic performance declines in a short time. Additionally, there exists a problem that a methane conversion rate (or a ratio of methane used to produce aromatic compounds and hydrogen) is low.

In view of the above, some processes for solving the above problems are disclosed in Patent Documents 1 to 9 and the like, in which a lower hydrocarbon aromatization catalyst on which molybdenum or a metal component consisting of molybdenum and other is loaded produces aromatic compounds from methane. According to such processes, reaction is made with the addition of hydrogen, carbon dioxide or carbon monoxide and therefore coking (carbon formation or methane-decomposing reaction) can be suppressed so as to maintain the catalytic activity for a long period of time. Particularly in a catalyst-producing process as disclosed in Patent Document 6, a metallosilicate is subjected to a surface treatment with silica so that the catalytic activity is stabilized.

However, a further development in such catalysts is desired in order to further improve the production efficiency of aromatic compounds and hydrogen, and additionally drawbacks have been encountered in the above conventional techniques. Even with the above conventional techniques, the formation rate of aromatic hydrocarbons (such as benzene) is currently not so high as to perfectly suppress the coke formation that gradually develops with a lapse of time. More specifically, a decrease in formation of aromatic hydrocarbons particularly benzene) is grown.

Patent document 1: Japanese Patent Provisional Publication No. 2005-254122
Patent document 2: Japanese Patent Provisional Publication No. 2005-254121
Patent document 3: Japanese Patent Provisional Publication No. 2006-263682
Patent document 4: Japanese Patent Provisional Publication No. 2005-254120
Patent document 5: Japanese Patent Provisional Publication No. 2006-263683
Patent document 6: Japanese Patent Provisional Publication No. 2007-014894
Patent document 7: Japanese Patent Provisional Publication No. 2005-255605
Patent document 8: International Publication No. WO05/028105
Patent document 9: International Publication No. WO06/011568

DISCLOSURE OF THE INVENTION

The present invention was made in view of the above situation. Its object is to provide an improved process of regenerating a catalyst for converting lower hydrocarbons into aromatic compounds, the process being able to remove carbon formed and accumulated bit by bit by the reaction producing aromatic hydrocarbons from lower hydrocarbons and to improve stability of the catalyst performance.

An aspect of the present invention resides in a process of regenerating an aromatizing catalyst for converting lower hydrocarbons into aromatic compounds. The process includes the steps of: (a) reacting the aromatizing catalyst with a hydrogen gas in an atmosphere containing the hydrogen gas after using the aromatizing catalyst in an aromatizing reaction for converting lower hydrocarbons into aromatic compounds; (b) decreasing a temperature of the atmosphere containing the hydrogen gas reacted with the aromatizing catalyst, by supplying one of an inert gas and a reducing gas to the atmosphere; (c) reacting the aromatizing catalyst whose atmosphere is decreased in temperature with an oxidizing gas; and (d) reacting the aromatizing catalyst reacted with the oxidizing gas, with a reducing gas. According to the present invention, it is allowed to remove carbon formed and accumulated bit by bit by the aromatizing reaction for producing aromatic hydrocarbons, at certain periods of time.

When reacting the aromatizing catalyst with the hydrogen gas, a temperature range is preferably equal to that applied during the aromatizing reaction.

When decreasing the temperature of the atmosphere containing the hydrogen gas, it is preferable that the temperature of the atmosphere is decreased by supplying the one of the inert gas and the reducing gas to the atmosphere so that the aromatizing catalyst has a temperature within a range of from 400 to 550° C.

When reacting the aromatizing catalyst with the oxidizing gas, it is preferable that the atmosphere to be reacted with the oxidizing gas is set to have a temperature within a range of from 450 to 500° C. With this, the aromatizing catalyst can be regenerated without declining a benzene formation rate and the stability of methane conversion rate.

The oxidizing gas is exemplified by those obtained by diluting oxygen gas with an inert gas so as to have an oxygen concentration of 2% v/v. Examples of the inert gas are helium gas, argon gas and nitrogen gas.

The reducing gas by which the temperature of the atmosphere is decreased includes, for example, hydrogen gas. On the other hand, examples of the reducing gas supplied when reacting the aromatizing catalyst therewith are methane, hydrogen gas, a mixture gas of methane and hydrogen, and the like.

According to the above-mentioned invention, it is allowed to regenerate the aromatizing catalyst for converting lower hydrocarbons into aromatic compounds, thereby improving the stability of catalytic performance.

BEST MODE FOR CARRYING OUT THE INVENTION

A process of producing an aromatizing catalyst for converting lower hydrocarbons into aromatic compounds, and a process for regenerating the aromatizing catalyst according to the present invention will be discussed.

1. Preparation of Catalyst Substrate

A powdered ZSM-5 ($SiO_2/Al_2O_3$=25 to 60, commercially available) of ammonium type is calcined in air at 700° C., thereby obtaining a HZSM-5 powder. Aminopropyl-triethoxysilane compound (hereinafter referred to as "APTES") was weighed to be 0.25 wt % in terms of $SiO_2$ based on the HZSM-5 zeolite dissolved in ethanol in order to suppress the acid point at the surface of the HZSM-5 zeolite, and then dissolved in a suitable amount of ethanol thereby preparing an immersion solution. Then, the HZSM-5 powder is added to the immersion solution with stirring at room temperature so as to be well impregnated with the immersion solution. Upon removing the ethanol component (or a solvent component) by spray drying, the resulting material is calcined at 550° C. for 6 hours to obtain a powdered 0.25% Si/HZSM-5 (HZSM-5 on which 0.25 wt % of Si is loaded).

2. Loading Metal Component on Catalyst Substrate

Then, the loading amount of a metal component, relative to the amount of the powdered 0.25% Si/HZSM-5, will be discussed.

Hexaammonium heptamolybdate hydrate compound is weighed and dissolved in a suitable amount of distilled water in such a manner that the loading amount of Mo on the powdered 0.25% Si/HZSM-5 is to be 6 wt %, thereby preparing an impregnation solution. The powdered 0.25% Si/HZSM-5 is added to the impregnation solution with stirring at room temperature so as to be well impregnated with the impregnation solution, upon which the water content of the solvent is removed by spray drying. The powdered 0.25% Si/HZSM-5 is thereafter calcined at 550° C. for 5 hours thereby obtaining a powdered 6% Mo/0.25% Si/HZSM-5 (HZSM-5 on which 6 wt % of Mo and 0.25 wt % of Si are loaded).

3. Extrusion

Extrusion or shaping is carried out as follows, thereby obtaining a catalyst formed into a cylindrical shape having an average diameter of 2.4 mm and a length of 5 mm.

(i) Composition

Composition of inorganic component alone: ZSM-5 (82.5%), clay (12.5%), and glass fiber (5%)

Total composition: the above-mentioned inorganic component (76.5%), an organic binder (17.3 wt %), and water content (24.3%)

(ii) Extrusion

The inorganic component, the organic binder and the water content are prepared to have the above-mentioned composition and then mixed or kneaded by using a kneader or the like.

Subsequently, the thus mixed substance is formed into a cylindrical shape (2.4 mm in average diameter and 5 mm in length) by using a vacuum extrusion machine. The extrusion pressure applied during this extrusion process is set within a range of from 2 to 8 MPa.

Normally, the catalyst substrate applied in hydrocarbon reformation is used as a fluidized bed catalyst in the form of particles having a particle diameter of from several to several hundreds of micrometers. Such a catalyst substrate is produced by mixing a catalyst substrate material with the organic binder, an inorganic binder (e.g., clay in general) and water thereby obtaining slurry, and then by pelletizing the slurry by spray drying (free from extrusion pressure), followed by calcination. In this case where there is no extrusion pressure, the amount of clay added as a calcination assistant in order to ensure a calcination velocity is within a range of from about 40 to 60 wt %. However, in the present invention in which the catalyst is shaped by the vacuum extrusion machine, i.e. by a high-pressure extrusion, it is allowed to reduce the amount of additives such as clay to a range of from 15 to 25 wt %. With this, the catalytic activity can be improved.

(iii) Drying and Calcination

Drying is carried out at 70° C. for 12 hours and then further carried out at 90° C. for about 36 hours, thereby removing the water content added in the extrusion or shaping process. Thereafter, calcination is conducted at temperature-increasing and temperature-decreasing rates ranging from 90 to 100° C./h. In order to remove the organic binder added in the extrusion process but not to instantaneously calcine it, about 2 to 6 hours of temperature retention within a temperature range of from 250 to 500° C. is performed twice. If the temperature-increasing and temperature-decreasing rates exceed the above-mentioned rate and if the retention time enough to remove the binder is not ensured, the binder is to calcine instantaneously so as to decrease the strength of the calcined substance. A calcination temperature is set within a range of from 550 to 800° C. This is because the calcination temperature of not higher than 550° C. decreases the strength of the calcined substance while that of not lower than 800° C. causes a property reduction.

4. Pretreatment for Catalyst

Thereafter, a pretreatment is carried out on the catalyst before activating it, in such a manner as to carburize the calcined substance at 700° C. by using a methane gas having a methane/hydrogen ratio of 1/4. With this, a molybdenum component is converted into molybdenum carbide so as to activate the catalyst to cause aromatization reaction. If the catalyst is calcined in air immediately before carburization treatment, a higher activity can be expected by the carburization treatment.

5. Aromatization Reaction of Lower Hydrocarbons

Figure 1:
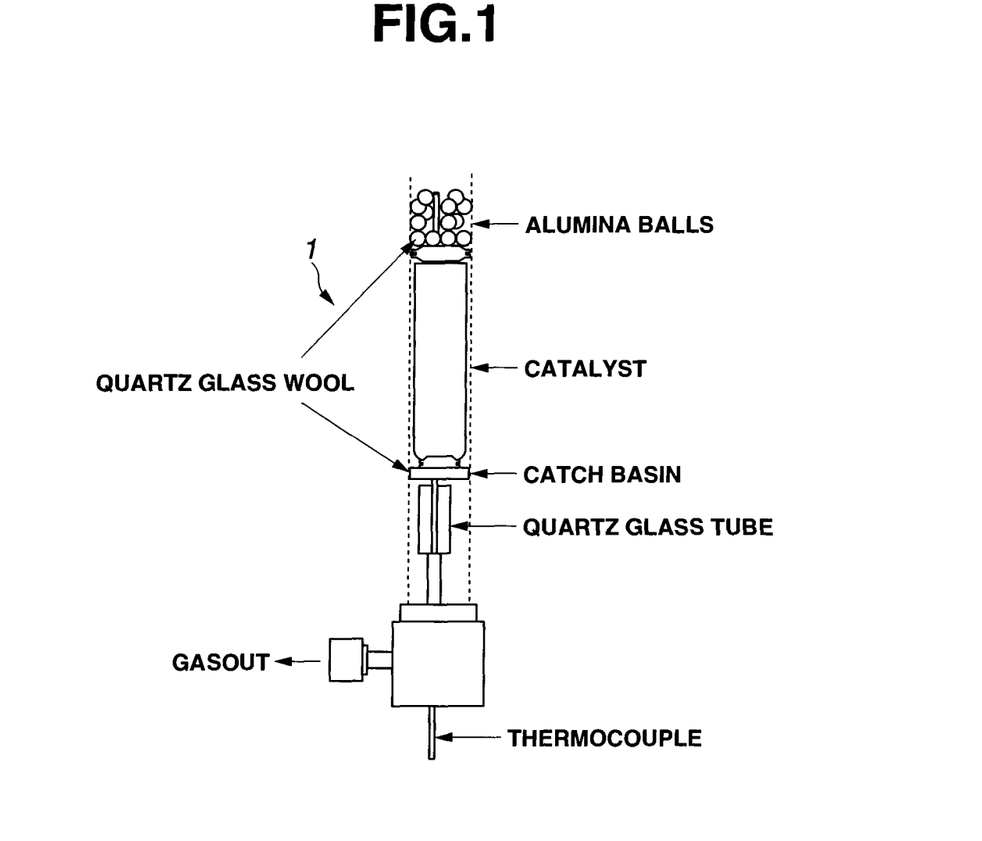
FIG. 1 is a schematic diagram of a fixed-bed reactor used to practice an embodiment of a process of regenerating a catalyst according to the present invention, the catalyst for converting lower hydrocarbons into aromatic compounds.

As shown in FIG. 1, the catalyst subjected to the carburization treatment and having an average diameter of 2.4 mm and a length of 5 mm is charged into a reaction tube of a fixed-bed reactor 1, the reaction tube having an internal diameter of 18 mm and being produced in such a manner as to make a calorizing treatment on an Inconel 800H's portion with which gas is to be brought into contact. Then the catalyst is reacted under the conditions as shown in Table 1.

TABLE 1

| Items | Reaction condition |
| --- | --- |
| Charged amount of catalyst | 14 g |
| Ratio of zeolite | 82.50% |
| Feed gas | 100$CH_4$ (methane) + 3$CO_2$ (carbonic acid gas) |

TABLE 1-continued

| Items | Reaction condition |
| --- | --- |
| Reaction space velocity | 3000 ml/g - MFI/h ($CH_4$ gas flow base) |
| Reaction temperature | 780° C. |
| Reaction pressure | 0.3 MPa |

The following description is directed to: a process for making a pretreatment on a catalyst according to the present invention, prior to carburization (referred to as "a pretreatment process"); a process for causing the catalyst to react (referred to as "a reaction process"); and a process for regenerating the catalyst (referred to as "a regeneration process").

(I) Pretreatment Process Made Prior to Carburization, and Reaction Process

Figure 2:
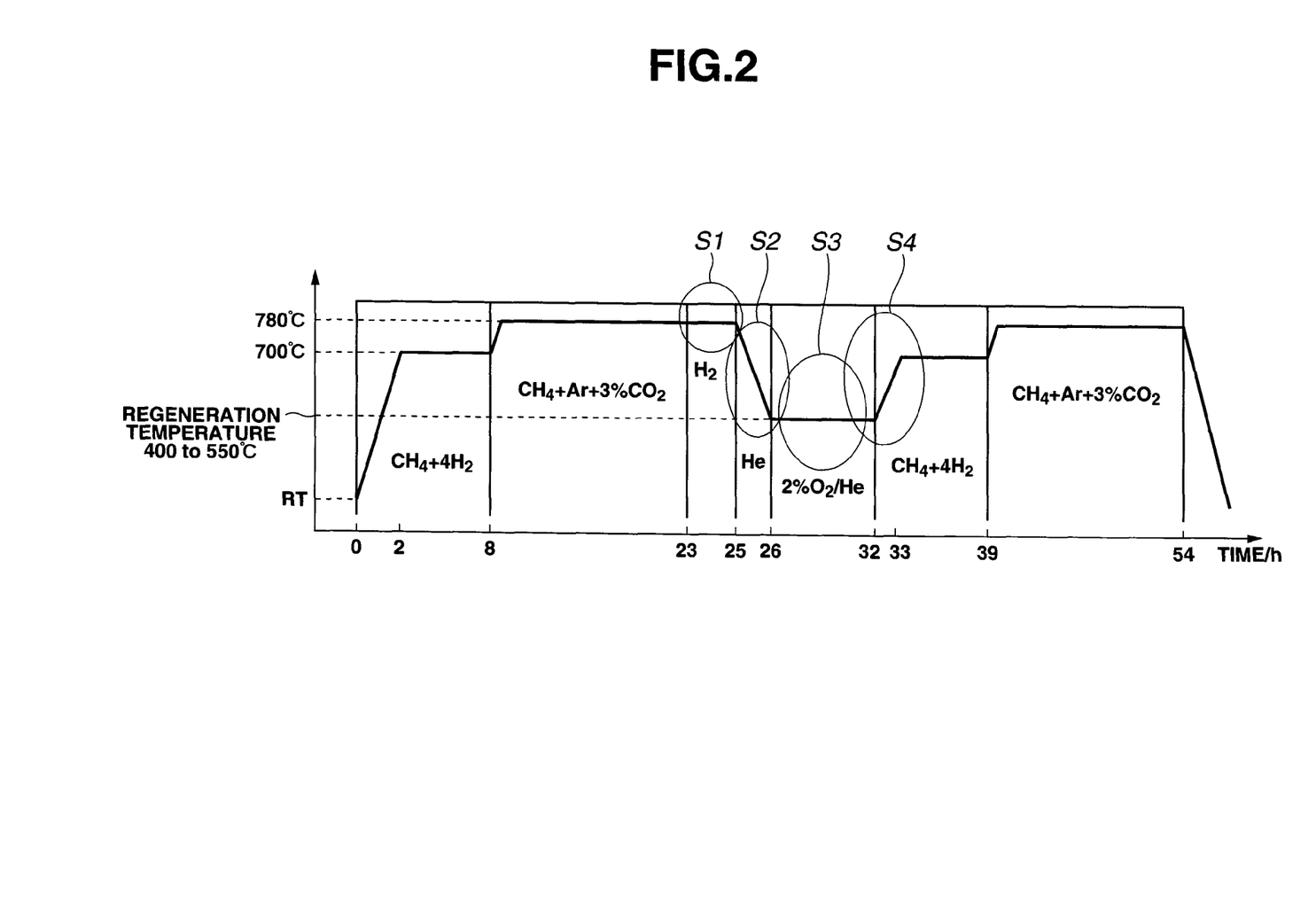
FIG. 2 is a time chart of processes conducted on the catalyst, including a pretreatment process made before carburization, a reaction process and a regeneration process.

According to a time chart in the pretreatment and reaction processes as shown in FIG. 2, catalyst regeneration and aromatization reaction are repeatedly carried out. In the pretreatment process, the reaction temperature is increased to 700° C. in an atmosphere of $CH_4+4H_2$ with taking 2 hours, and held there for 6 hours. The molybdenum component carburized by this process comes to belong to an active species. In the aromatization reaction process, 3% of carbon dioxide is added to methane used as a lower hydrocarbon, for the purpose of stabilizing the reaction. Then, reaction products are analyzed by gas chromatography in which argon gas (a rare gas not pertinent to the reaction) serving as an internal standard for calibrating analysis is mixed with methane serving as a reaction gas, in a mixture ratio of 10:100. Upon making a regenerating treatment after the aromatization reaction (or a primary reaction), a further aromatization reaction (or a secondary reaction) was carried out and then reaction properties are evaluated. The primary and secondary aromatization reactions are made for 15 hours each.

(II) Regeneration Process

Regeneration of the catalyst was performed in four steps as shown in the time chart of FIG. 2.

In the first step (S1), regeneration is performed by hydrogen gas for 2 hours at the same temperature as the reaction conditions. With this, coke having a high hydrocarbon component to be easily removable can be removed.

In the second step (S2), the temperature is decreased to a range of from 400 to 550° C. If air, oxygen or other oxidizing gas is used as a gas relating to the second step, carbon combustion is to be abruptly evolved thereby heating the catalyst abnormally to destroy zeolite, and additionally molybdenum carbide is to be instantaneously oxidized to be molybdenum oxide and sublimated. Therefore, an inert gas or reducing gas is used as the gas relating to the second step. Though helium gas was used as the inert gas in Examples and Comparative Examples, argon gas or nitrogen gas also provides the same effects. Examples of the reducing gas include hydrogen gas. When methane gas is used as the reducing gas, coking can possibly occur.

In the third step (S3), the catalyst is slowly burned over 6 hours by oxygen gas diluted with the inert gas to a low concentration (2%), with which cokes having a high carbonaceous component and a low hydrocarbon component so as to be resistant to burning is oxidized and removed. An atmosphere of high oxygen concentration, such as air (20.9% oxygen concentration) is not preferable since abrupt carbon combustion is caused thereby abnormally heating the catalyst and destroying zeolite and additionally molybdenum carbide is instantaneously oxidized to be molybdenum oxide and sublimated.

There is a possibility in the third step that the molybdenum active species obtained in carburization as the pretreatment process is oxidized again to return to molybdenum oxide.

In the fourth step (S4), the catalyst is therefore increased in temperature to 700° C. in an atmosphere of $CH_4+4H_2$ and then held at the temperature thereby being subjected to the second carburization treatment, for the purpose of carburizing the molybdenum component (which might return to molybdenum oxide) again so as to convert it into molybdenum carbide that can serve as the active species. In the fourth step the temperature-increasing is not required to start from room temperature to 700° C. as the first carburization pretreatment process, and may start from the regeneration temperature applied in the third step (i.e. 400 to 550° C.) to 700° C. This is because carburization of molybdenum is achieved only by keeping a temperature of 700° C. for a certain period of time in the atmosphere of $CH_4+4H_2$. The catalyst carburized again can serve the secondary aromatization reaction.

Examples and comparative examples of a process of regenerating a catalyst for converting lower hydrocarbons into aromatic compounds according to the invention are shown in the following.

Comparative Example 1

A catalyst obtained upon the carburization treatment based on the above-mentioned pretreatment process made before activating the catalyst was charged into a reaction tube of a fixed-bed reactor 1 as shown in FIG. 1, on which a primary reaction for aromatizing methane was made under the reaction conditions as shown in Table 1, followed by studying time variations in a methane conversion rate and a benzene formation rate.

Subsequently, the catalyst that had served the aromatization reaction was regenerated by the regeneration process as mentioned above with the exception that the third step (S3) in the regeneration process, made in an oxygen atmosphere, was carried out at a temperature of 400° C. The catalyst thus regenerated by the regeneration process was charged into the reaction tube of the fixed-bed reactor 1 as shown in FIG. 1, on which a secondary reaction for aromatizing methane was made under the reaction conditions as shown in Table 1, followed by studying time variations in the methane conversion rate and the benzene formation rate. The methane conversion rate and the benzene formation rate are defined as follows (they are the same in the explanations of Comparative Example 2, Example 1 and Example 2).

Methane conversion rate=("a flow rate of feedstock methane"−"a flow rate of unreacted methane")/ "the flow rate of feedstock methane"×100

Benzene formation rate="the number of nmol of benzene produced by 1 g of the catalyst per second"

Comparative Example 2

A catalyst obtained upon the carburization treatment based on the above-mentioned pretreatment process made before activating the catalyst was charged into a reaction tube of a fixed-bed reactor 1 as shown in FIG. 1, on which a primary reaction for aromatizing methane was made under the reaction conditions as shown in Table 1, followed by studying time variations in a methane conversion rate and a benzene formation rate.

Subsequently, the catalyst that had served the aromatization reaction was regenerated by the regeneration process as mentioned above with the exception that the third step (S3) in the regeneration process, made in an oxygen atmosphere, was carried out at a temperature of 550° C. The catalyst thus regenerated by the regeneration process was charged into the reaction tube of the fixed-bed reactor 1 as shown in FIG. 1, on which a secondary reaction for aromatizing methane was made under the reaction conditions as shown in Table 1, followed by studying time variations in the methane conversion rate and the benzene formation rate.

Example 1

A catalyst obtained upon the carburization treatment based on the above-mentioned pretreatment process made before activating the catalyst was charged into a reaction tube of a fixed-bed reactor 1 as shown in FIG. 1, on which a primary reaction for aromatizing methane was made under the reaction conditions as shown in Table 1, followed by studying time variations in a methane conversion rate and a benzene formation rate.

Subsequently, the catalyst that had served the aromatization reaction was regenerated by the regeneration process as mentioned above with the exception that the third step (S3) in the regeneration process, made in an oxygen atmosphere, was carried out at a temperature of 500° C. The catalyst thus regenerated by the regeneration process was charged into the reaction tube of the fixed-bed reactor 1 as shown in FIG. 1, on which a secondary reaction for aromatizing methane was made under the reaction conditions as shown in Table 1, followed by studying time variations in the methane conversion rate and the benzene formation rate.

Example 2

A catalyst obtained upon the carburization treatment based on the above-mentioned pretreatment process made before activating the catalyst was charged into a reaction tube of a fixed-bed reactor 1 as shown in FIG. 1, on which a primary reaction for aromatizing methane was made under the reaction conditions as shown in Table 1, followed by studying time variations in a methane conversion rate and a benzene formation rate.

Subsequently, the catalyst that had served the aromatization reaction was regenerated by the regeneration process as mentioned above with the exception that the third step (S3) in the regeneration process, made in an oxygen atmosphere, was carried out at a temperature of 450° C. The catalyst thus regenerated by the regeneration process was charged into the reaction tube of the fixed-bed reactor 1 as shown in FIG. 1, on which a secondary reaction for aromatizing methane was made under the reaction conditions as shown in Table 1, followed by studying time variations in the methane conversion rate and the benzene formation rate.

Figure 3:
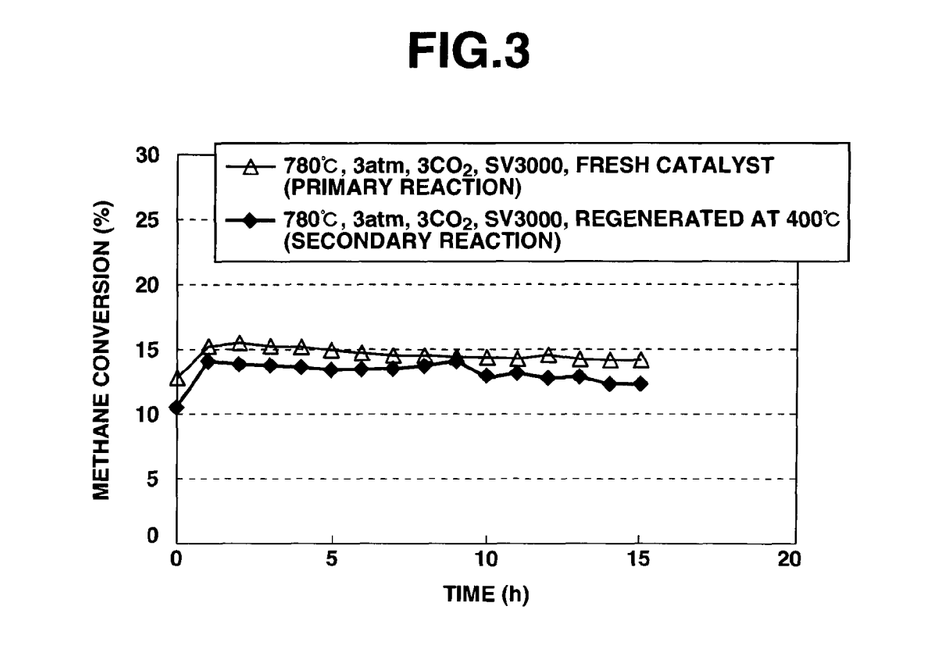
FIG. 3 shows a time variation in a methane conversion rate of a primary methane aromatization reaction made at 780° C., 3 atm and a space velocity of 3000 with a fresh catalyst and a feed gas represented by $100CH_4+3CO_2$, and additionally shows a time variation in the methane conversion rate of a secondary methane aromatization reaction made at 780° C., 3 atm and a space velocity of 3000 with a feed gas represented by $100CH_4+3CO_2$ and with a catalyst regenerated at 400° C. according to the regeneration process of Comparative Example 1.

FIG. 3 shows a time variation in the methane conversion rate of the primary methane aromatization reaction made at 780° C., 3 atm and a space velocity of 3000 with a fresh catalyst and a feed gas represented by $100CH_4+3CO_2$. Additionally, FIG. 3 further shows a time variation in the methane conversion rate of the secondary methane aromatization reaction made at 780° C., 3 atm and a space velocity of 3000 with a feed gas represented by $100CH_4+3CO_2$ and with the catalyst regenerated at 400° C. according to the regeneration process employed in Comparative Example 1.

Figure 4:
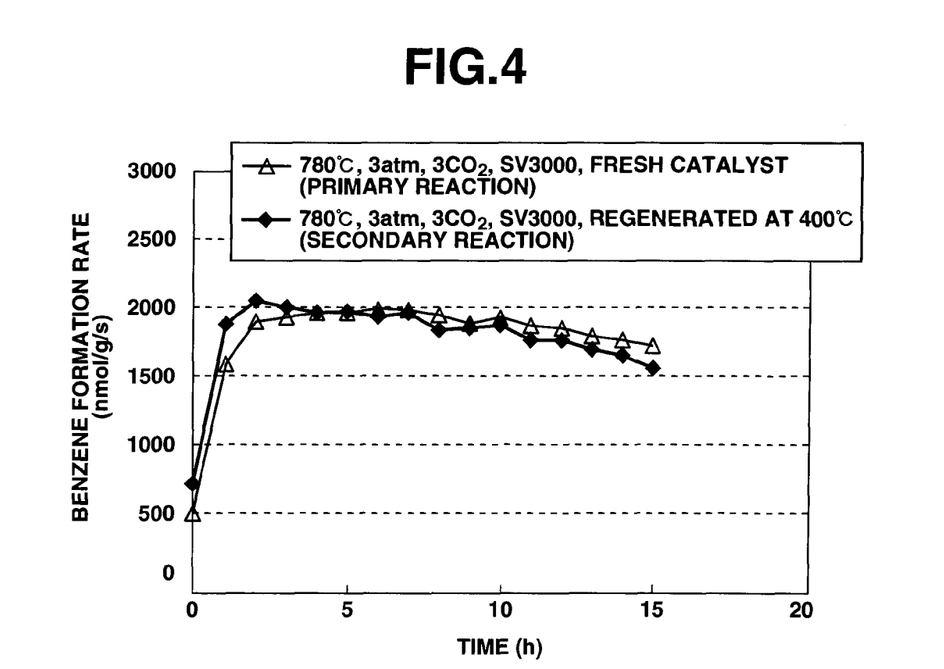
FIG. 4 shows a time variation in a benzene formation rate of a primary methane aromatization reaction made at 780° C., 3 atm and a space velocity of 3000 with a fresh catalyst and a feed gas represented by $100CH_4+3CO_2$, and additionally shows a time variation in the benzene formation rate of a secondary methane aromatization reaction made at 780° C., 3 atm and a space velocity of 3000 with a feed gas represented by $100CH_4+3CO_2$ and with a catalyst regenerated at 400° C. according to the regeneration process of Comparative Example 1.

FIG. 4 shows a time variation in the benzene formation rate of the primary methane aromatization reaction made at 780° C., 3 atm and a space velocity of 3000 with a fresh catalyst and a feed gas represented by $100CH_4+3CO_2$. Additionally, FIG. 4 further shows a time variation in the benzene formation rate of the secondary methane aromatization reaction made at 780° C., 3 atm and a space velocity of 3000 with a feed gas represented by $100CH_4+3CO_2$ and with the catalyst regenerated at 400° C. according to the regeneration process employed in Comparative Example 1.

In comparison between the primary methane aromatization reaction and the secondary one made after the regenerating treatment of Comparative Example 1 at 400° C., by reference to FIG. 3, the methane conversion rate is kept stable. This is considered to be an effect produced by carrying out the treatment of the first step (S1) of the regeneration process in the hydrogenous atmosphere. However, by reference to property plots of FIGS. 3 and 4, it is apparent that the secondary aromatization reaction made after regeneration is lower than the primary one in terms of both the methane conversion rate and the benzene formation rate. This means that the low temperature applied in the oxygenous atmosphere of the third step (S3) of the regeneration process is inadequate, while meaning the effect produced by carrying out the treatment of the first step (S1) of the regeneration process in the hydrogenous atmosphere.

Figure 5:
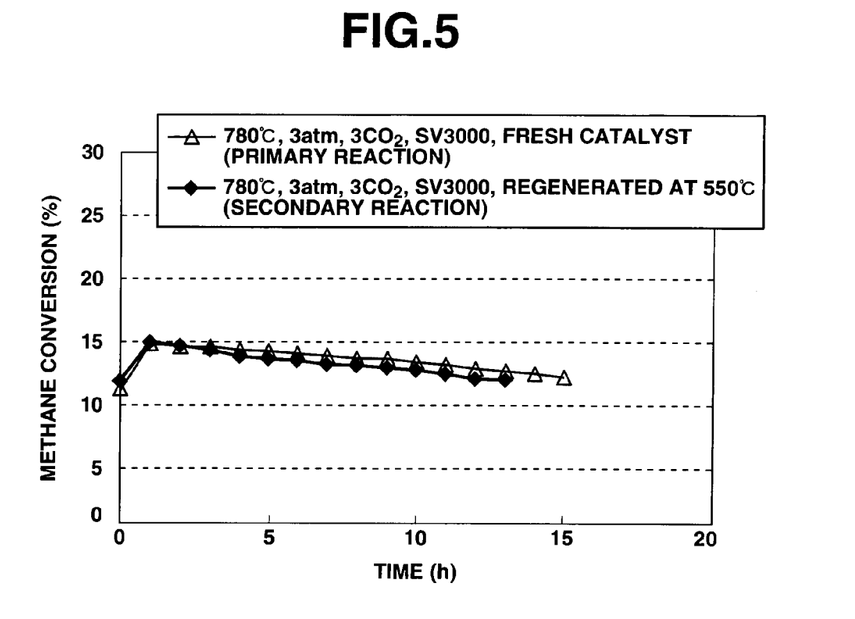
FIG. 5 shows a time variation in a methane conversion rate of a primary methane aromatization reaction made at 780° C., 3 atm and a space velocity of 3000 with a fresh catalyst and a feed gas represented by $100CH_4+3CO_2$, and additionally shows a time variation in the methane conversion rate of a secondary methane aromatization reaction made at 780° C., 3 atm and a space velocity of 3000 with a feed gas represented by $100CH_4+3CO_2$ and with a catalyst regenerated at 550° C. according to the regeneration process of Comparative Example 2.

FIG. 5 shows a time variation in the methane conversion rate of the primary methane aromatization reaction made at 780° C., 3 atm and a space velocity of 3000 with a fresh catalyst and a feed gas represented by $100CH_4+3CO_2$. Additionally, FIG. 5 further shows a time variation in the methane conversion rate of the secondary methane aromatization reaction made at 780° C., 3 atm and a space velocity of 3000 with a feed gas represented by $100CH_4+3CO_2$ and with the catalyst regenerated at 550° C. according to the regeneration process employed in Comparative Example 2.

Figure 6:
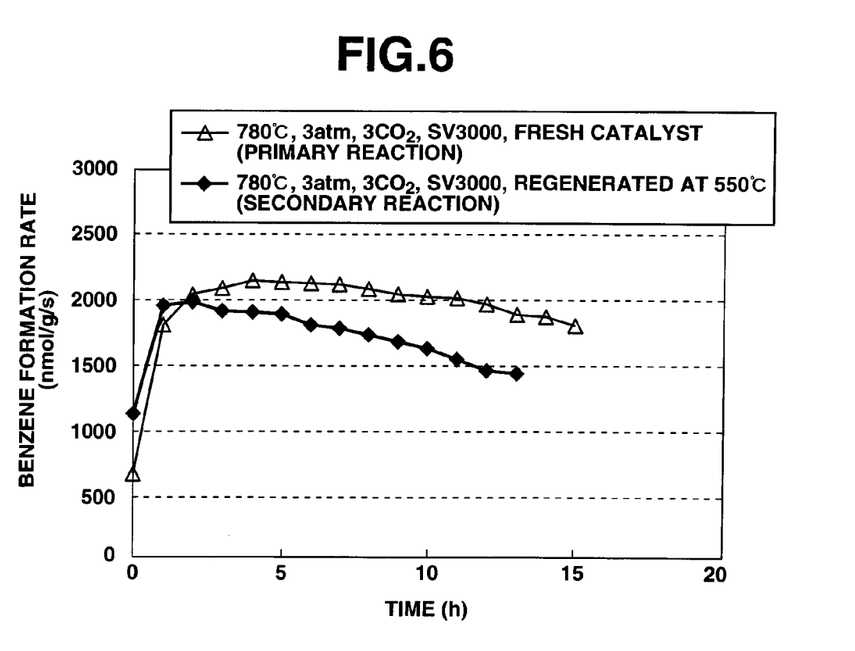
FIG. 6 shows a time variation in a benzene formation rate of a primary methane aromatization reaction made at 780° C., 3 atm and a space velocity of 3000 with a fresh catalyst and a feed gas represented by $100CH_4+3CO_2$, and additionally shows a time variation in the benzene formation rate of a secondary methane aromatization reaction made at 780° C., 3 atm and a space velocity of 3000 with a feed gas represented by $100CH_4+3CO_2$ and with a catalyst regenerated at 550° C. according to the regeneration process of Comparative Example 2.

FIG. 6 shows a time variation in the benzene formation rate of the primary methane aromatization reaction made at 780° C., 3 atm and a space velocity of 3000 with a fresh catalyst and a feed gas represented by $100CH_4+3CO_2$. Additionally, FIG. 6 further shows a time variation in the benzene formation rate of the secondary methane aromatization reaction made at 780° C., 3 atm and a space velocity of 3000 with a feed gas represented by $100CH_4+3CO_2$ and with the catalyst regenerated at 550° C. according to the regeneration process employed in Comparative Example 2.

In comparison between the primary methane aromatization reaction and the secondary one made after the regenerating treatment conducted according to Comparative Example 1 with the exception that the third step of the oxygenous atmosphere was carried out at 550° C., by reference to FIGS. 5 and 6, it is found that the effect produced from the treatment in the hydrogenous atmosphere of the first step (S1) is exerted and that the methane conversion rate is kept stable. However, the secondary reaction is lower than the primary one in terms of both the methane conversion rate and the benzene formation rate, as in the case of Comparative Example 1, and additionally is significantly lowered particularly in benzene formation rate. With this, it is considered that the regeneration temperature of 550° C. is excessively high.

Figure 7:
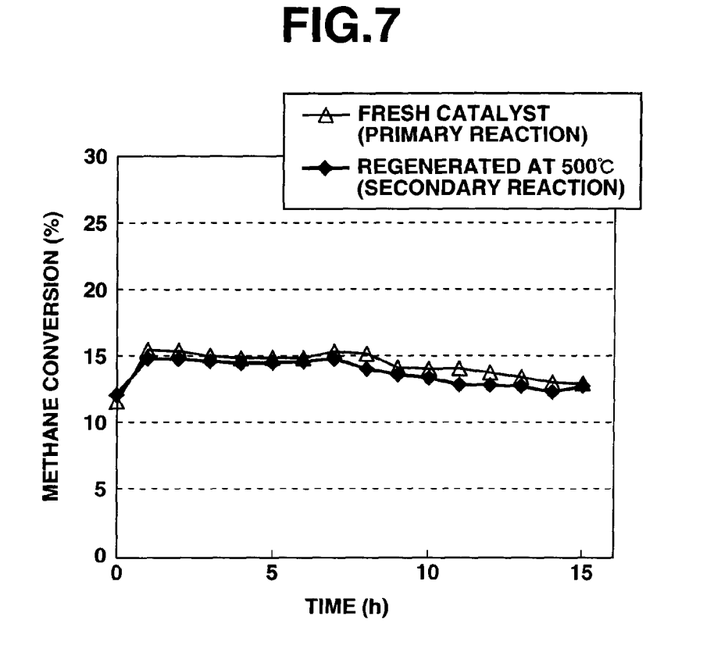
FIG. 7 shows a time variation in a methane conversion rate of a primary methane aromatization reaction made at 780° C., 3 atm and a space velocity of 3000 with a fresh catalyst and a feed gas represented by $100CH_4+3CO_2$, and additionally shows a time variation in the methane conversion rate of a secondary methane aromatization reaction made at 780° C., 3 atm and a space velocity of 3000 with a feed gas represented by $100CH_4+3CO_2$ and with a catalyst regenerated at 500° C. according to the regeneration process of Example 1.

FIG. 7 shows a time variation in the methane conversion rate of the primary methane aromatization reaction made at 780° C., 3 atm and a space velocity of 3000 with a fresh catalyst and a feed gas represented by $100CH_4+3CO_2$. Additionally, FIG. 7 further shows a time variation in the methane conversion rate of the secondary methane aromatization reaction made at 780° C., 3 atm and a space velocity of 3000 with a feed gas represented by $100CH_4+3CO_2$ and with the catalyst regenerated at 500° C. according to the regeneration process employed in Example 1.

Figure 8:
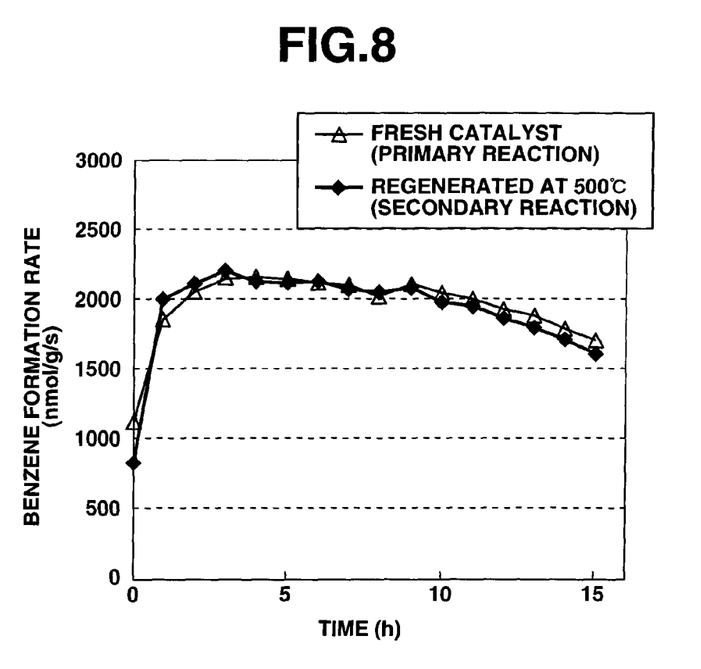
FIG. 8 shows a time variation in a benzene formation rate of a primary methane aromatization reaction made at 780° C., 3 atm and a space velocity of 3000 with a fresh catalyst and a feed gas represented by $100CH_4+3CO_2$, and additionally shows a time variation in the benzene formation rate of a secondary methane aromatization reaction made at 780° C., 3 atm and a space velocity of 3000 with a feed gas represented by $100CH_4+3CO_2$ and with a catalyst regenerated at 500° C. according to the regeneration process of Example 1.

FIG. 8 shows a time variation in the benzene formation rate of the primary methane aromatization reaction made at 780° C., 3 atm and a space velocity of 3000 with a fresh catalyst and a feed gas represented by $100CH_4+3CO_2$. Additionally, FIG. 8 further shows a time variation in the benzene formation rate of the secondary methane aromatization reaction made at 780° C., 3 atm and a space velocity of 3000 with a feed gas represented by $100CH_4+3CO_2$ and with the catalyst regenerated at 500° C. according to the regeneration process employed in Example 1.

Figure 9:
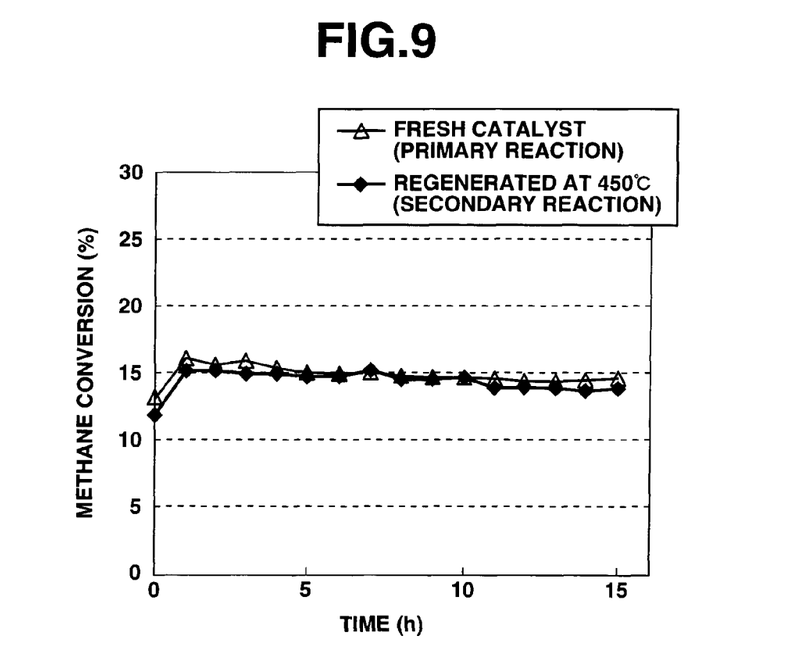
FIG. 9 shows a time variation in a methane conversion rate of a primary methane aromatization reaction made at 780° C., 3 atm and a space velocity of 3000 with a fresh catalyst and a feed gas represented by $100CH_4+3CO_2$, and additionally shows a time variation in the methane conversion rate of a secondary methane aromatization reaction made at 780° C., 3 atm and a space velocity of 3000 with a feed gas represented by $100CH_4+3CO_2$ and with a catalyst regenerated at 450° C. according to the regeneration process of Example 2.

FIG. 9 shows a time variation in the methane conversion rate of the primary methane aromatization reaction made at 780° C., 3 atm and a space velocity of 3000 with a fresh catalyst and a feed gas represented by $100CH_4+3CO_2$. Additionally, FIG. 9 further shows a time variation in the methane conversion rate of the secondary methane aromatization reaction made at 780° C., 3 atm and a space velocity of 3000 with a feed gas represented by $100CH_4+3CO_2$ and with the catalyst regenerated at 450° C. according to the regeneration process employed in Example 2.

Figure 10:
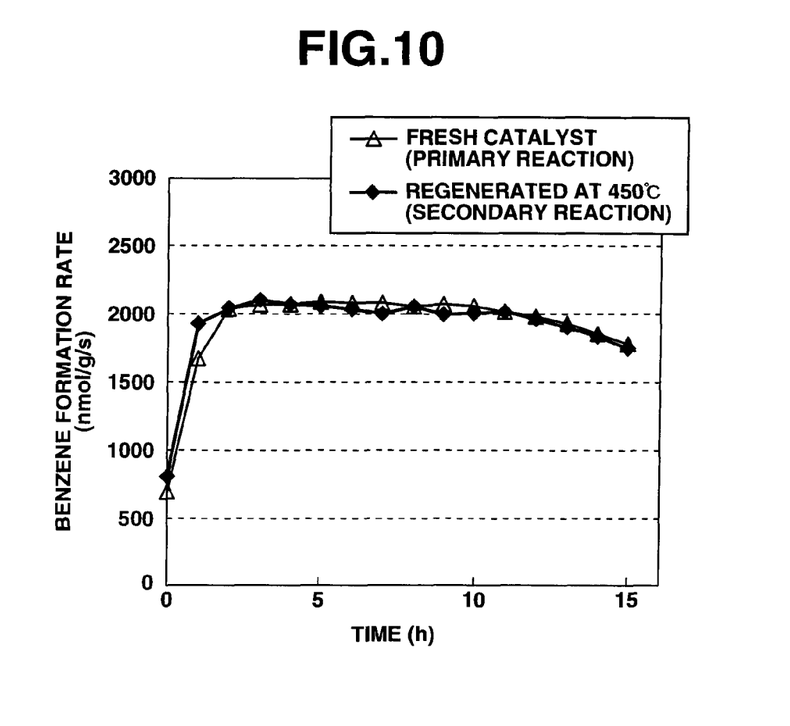
FIG. 10 shows a time variation in a benzene formation rate of a primary methane aromatization reaction made at 780° C., 3 atm and a space velocity of 3000 with a fresh catalyst and a feed gas represented by $100CH_4+3CO_2$, and additionally shows a time variation in the benzene formation rate of a secondary methane aromatization reaction made at 780° C., 3 atm and a space velocity of 3000 with a feed gas represented by $100CH_4+3CO_2$ and with a catalyst regenerated at 450° C. according to the regeneration process of Example 2.

FIG. 10 shows a time variation in the benzene formation rate of the primary methane aromatization reaction made at 780° C., 3 atm and a space velocity of 3000 with a fresh catalyst and a feed gas represented by $100CH_4+3CO_2$. Additionally, FIG. 10 further shows a time variation in the benzene formation rate of the secondary methane aromatization reaction made at 780° C., 3 atm and a space velocity of 3000 with a feed gas represented by $100CH_4+3CO_2$ and with the catalyst regenerated at 450° C. according to the regeneration process employed in Example 2.

As apparent from property plots of FIGS. 7 to 10, it is confirmed that the aromatizing catalyst can be effectively regenerated without declining the benzene formation rate and the stability in methane conversion rate when the regeneration temperature applied in the third step of the catalyst regeneration process is 450 or 500° C. It is also found that the effect is sufficiently obtained even if the atmosphere in the third step of the regeneration process has a low oxygen concentration, i.e. an oxygen concentration of 2%.

The invention claimed is:

1. A process of regenerating an aromatizing catalyst for converting lower hydrocarbons into aromatic compounds, comprising the steps of:
   reacting the aromatizing catalyst with a hydrogen gas in an atmosphere containing at least the hydrogen gas after using the aromatizing catalyst in an aromatizing reaction for converting lower hydrocarbons into aromatic compounds;
   decreasing a temperature of the atmosphere containing the hydrogen gas reacted with the aromatizing catalyst to a decreased temperature by supplying one of an inert gas and a reducing gas to the atmosphere;
   reacting the aromatizing catalyst with an oxidizing gas while the atmosphere remains decreased in temperature, wherein the oxidizing gas comprises an inert gas and an oxygen gas, and an oxygen concentration of the oxidizing gas is 2% v/v; and
   after the step of reacting the aromatizing catalyst with the oxidizing gas, reacting the aromatizing catalyst with a reducing gas.

2. A process of regenerating an aromatizing catalyst for converting lower hydrocarbons into aromatic compounds, as claimed in claim 1, wherein a temperature range applied during reacting the aromatizing catalyst with the hydrogen gas is equal to that applied during the aromatizing reaction.

3. A process of regenerating an aromatizing catalyst for converting lower hydrocarbons into aromatic compounds, as claimed in claim 1, wherein the decreased temperature is within a range of from 400 to 550° C.

4. A process of regenerating an aromatizing catalyst for converting lower hydrocarbons into aromatic compounds, as claimed in claim 1, wherein the decreased temperature is within a range of from 450 to 500° C.

* * * * *